(12) United States Patent
Browning

(10) Patent No.: US 6,805,136 B2
(45) Date of Patent: Oct. 19, 2004

(54) HAIR RELAXER

(75) Inventor: Paul T. Browning, Trafalgar, IN (US)

(73) Assignee: Kenra, LLC, Indianapolis, IN (US)

( * ) Notice: Subject to any disclaimer, the term of this patent is extended or adjusted under 35 U.S.C. 154(b) by 27 days.

(21) Appl. No.: 10/002,487

(22) Filed: Nov. 2, 2001

(65) Prior Publication Data

US 2003/0098034 A1 May 29, 2003

(51) Int. Cl.$^7$ .................................................. A45D 7/04
(52) U.S. Cl. ........................................ 132/205; 132/204
(58) Field of Search ................................. 132/205, 200, 132/202, 206, 211, 204; 424/70.4, 70.2, 70.41

(56) References Cited

U.S. PATENT DOCUMENTS

| | | | |
|---|---|---|---|
| 2,350,178 A | | 5/1944 | Martin |
| 2,418,664 A | | 4/1947 | Ramsey |
| 3,533,417 A | | 10/1970 | Bartoszewicz et al. |
| 3,672,375 A | | 6/1972 | Kalopissis et al. |
| 3,910,289 A | | 10/1975 | Wajaroff et al. |
| 3,912,808 A | | 10/1975 | Sokol |
| 3,971,391 A | * | 7/1976 | Bore et al. ..................... 424/70 |
| 3,973,574 A | | 8/1976 | Minagawa, deceased et al. |
| 3,996,146 A | | 12/1976 | Tarasov et al. |
| 4,027,008 A | | 5/1977 | Sokol |
| 4,134,411 A | | 1/1979 | Yamazaki |
| 4,175,572 A | | 11/1979 | Hsiung et al. |
| 4,240,450 A | | 12/1980 | Grollier et al. |
| 4,275,748 A | | 6/1981 | Graziano |
| 4,303,085 A | | 12/1981 | de la Guardia et al. |
| 4,304,244 A | | 12/1981 | de la Guardia |
| 4,313,933 A | | 2/1982 | Yamazaki |
| 4,314,572 A | | 2/1982 | de la Guardia et al. |
| 4,324,263 A | | 4/1982 | de la Guardia |
| 4,327,751 A | | 5/1982 | Evans |
| 4,349,537 A | | 9/1982 | Forbriger, Jr. |
| 4,361,157 A | | 11/1982 | James |
| 4,373,540 A | | 2/1983 | de la Guardia |
| 4,381,920 A | | 5/1983 | Garlen |
| 4,416,296 A | | 11/1983 | Meyers |
| 4,524,787 A | * | 6/1985 | Khalil ........................ 132/205 |
| 4,602,648 A | | 7/1986 | Syed et al. |
| 4,630,621 A | | 12/1986 | Pontani |
| 4,770,872 A | | 9/1988 | Hsiung et al. |
| 4,770,873 A | | 9/1988 | Wolfram et al. |
| 4,772,462 A | | 9/1988 | Boothe et al. |
| 4,781,724 A | | 11/1988 | Wajaroff et al. |
| 4,828,750 A | | 5/1989 | Simion et al. |
| 4,844,886 A | | 7/1989 | Hartmann et al. |
| 4,855,130 A | | 8/1989 | Konrad et al. |
| 4,898,726 A | | 2/1990 | Beste |
| 4,950,485 A | * | 8/1990 | Akhtar et al. ................. 424/71 |
| 4,982,749 A | | 1/1991 | Baker et al. |
| 4,982,750 A | | 1/1991 | Kaitz |
| 4,992,267 A | | 2/1991 | DenBeste et al. |
| 5,002,761 A | | 3/1991 | Mueller et al. |
| 5,068,101 A | | 11/1991 | Akhtar et al. |
| 5,148,822 A | | 9/1992 | Akhtar |
| 5,161,553 A | | 11/1992 | Cohen et al. |
| 5,293,885 A | | 3/1994 | Darkwa et al. |
| 5,294,230 A | | 3/1994 | Wu et al. |
| 5,376,364 A | | 12/1994 | Darkwa et al. |
| 5,503,826 A | | 4/1996 | Lang et al. |
| 5,520,909 A | | 5/1996 | Salce et al. |
| 5,562,110 A | | 10/1996 | Ottenbrite et al. |
| 5,609,859 A | | 3/1997 | Cowsar |
| 5,635,170 A | | 6/1997 | Lang et al. |
| 5,679,327 A | * | 10/1997 | Darkwa et al. ............ 424/70.4 |
| 6,125,856 A | | 10/2000 | Yamashita |

FOREIGN PATENT DOCUMENTS

| | | |
|---|---|---|
| EP | 1 603 321 | 11/1981 |
| EP | 1 603 322 | 11/1981 |
| EP | 1 603 323 | 11/1981 |
| EP | 1 603 324 | 11/1981 |
| EP | 0 083 095 A2 | 7/1983 |
| EP | 0 167 866 A2 | 1/1986 |
| EP | 0 190 834 A2 | 8/1986 |
| EP | 0 256 462 A2 | 2/1988 |
| EP | 0 257 256 A2 | 3/1988 |
| EP | 0 260 716 A1 | 3/1988 |
| EP | 0 328 816 A2 | 8/1989 |
| GB | 2 066 864 A | 7/1981 |
| GB | 2 068 031 A | 8/1981 |
| GB | 2 086 443 A | 5/1982 |
| GB | 2 090 303 A | 7/1982 |
| GB | 2 109 832 A | 6/1983 |
| GB | 2 114 616 A | 8/1983 |
| GB | 2 141 454 A | 12/1984 |
| JP | 2-76807 | 3/1990 |
| WO | WO 86/01403 | 3/1986 |
| WO | WO 88/00186 | 1/1988 |
| WO | WO 88/00464 | 1/1988 |
| WO | WO 88/02997 | 5/1988 |

OTHER PUBLICATIONS

Starch, M., "Silicones for Conditioning Damaged Hair," Soap/Cosmetics/Chemical Specialties, pp. 34–39, Apr., 1986.

"MERQUAT® 280," Bulletin 30–160C, Calgon Corporation, date unknown, 1 page.

"DOW CORNING® Q2–7224 Conditioning Agent", Technical Bulletin Form No. 22–956–83, Dow Corning Corporation, 1983, 4 pages.

* cited by examiner

Primary Examiner—Kevin Shaver
Assistant Examiner—Robyn Kieu Doan
(74) Attorney, Agent, or Firm—Bose McKinney & Evans LLP

(57) ABSTRACT

The present invention includes a hair relaxing composition for the straightening of hair. The composition includes a calcium hydroxide and guanidine carbonate. The present invention further includes a method for using the hair relaxing composition with the addition of heat to straighten hair.

62 Claims, No Drawings

HAIR RELAXER

FIELD OF THE INVENTION

The present invention relates to a method and composition for the straightening of hair.

BACKGROUND

Hair straightening or hair relaxing products have been commercially available for over forty years for people who want straighter more manageable hair. Most commercially available hair relaxers are composed of a strong hydroxide base that breaks the bonds in the hair. The African American consumer is the primary consumer of hydroxide hair straighteners. This type of product has enjoyed widespread success in the professional salon as well as the general consumer markets for over forty years for such consumers. However, hydroxide hair straighteners have not been successful in Caucasian and multi cultural salons. The failure of hydroxide-type hair straighteners to be successful for Caucasian and multi-cultural salons is due in part to the fact that hydroxide-type hair straighteners are too aggressive for this segment of the market. The rate at which these straighteners process on hair is too fast for Caucasian salon stylists to control.

The skill required to apply the product to hair, section by section, then work the product through the hair while staying within the prescribed time limits is a task that some salon stylists are not skilled enough to execute properly. Because there are few Caucasian patrons requiring hair straightening, Caucasian stylists do not have enough patrons to become skilled at applying the existing product within the time limits. Thus there are increased instances in which the skin is sensitized when hydroxide-type hair relaxers are used in Caucasian and multi cultural salons.

U.S. Pat. No. 4,304,244 discloses a guanidine hydroxide composition used to straighten hair. U.S. Pat. No. 4,304,244 discloses a guanidine salt such as guanidine carbonate that is mixed with an alkaline earth metal hydroxide such as calcium hydroxide to form guanidine hydroxide for use in straightening hair. Guanidine hydroxide is not stable for long periods of time. Therefore, the guanidine carbonate and calcium hydroxide must be mixed immediately before the hair relaxing treatment begins and the composition must be applied to and removed from the hair within a short period of time, i.e., before the composition becomes unstable e.g., within about four (4) hours. Although guanidine hydroxide has proven to be an effective hair straightening composition, the composition can only be in contact with the hair for a very limited amount of time or severe hair damage can result. The hair stylist applying the hair relaxing composition must work very quickly and possess a high degree of skill to successfully use most commercial hair relaxers. Furthermore, most commercial hair relaxers have a high pH and a tendency to cause skin and scalp irritation.

Commercial products based only on alkaline metal hydroxides such as sodium hydroxide and lithium hydroxide have also been used to straighten or relax unstraight hair. There are primarily four different types of alkaline metal hydroxide hair straighteners in use: barium hydroxide, lithium hydroxide, sodium hydroxide, and potassium hydroxide. The straightening product is usually applied quickly and can only remain in the hair for a very limited amount of time. If the product is not rinsed from hair at the appropriate time damage to the hair can occur as well as chemical burns to the scalp and areas surrounding the hair.

SUMMARY OF THE INVENTION

The present invention is a composition and method for straightening hair.

In one exemplary embodiment, a method of straightening hair comprising the steps of applying a composition to hair, the composition including an alkaline earth metal hydroxide and guanidine carbonate wherein the alkaline earth metal hydroxide is selected from the group consisting of calcium hydroxide, sodium hydroxide, barium hydroxide, lithium hydroxide, and potassium hydroxide, heating the composition and hair, and removing the composition from the hair. In one variation the alkaline earth metal hydroxide is included in an emulsion. In another variation the guanidine carbonate is included in an aqueous solution. In a further variation the alkaline earth metal hydroxide has a concentration of about 1.21% by weight to about 3.45% by weight, based on the total weight of the emulsion. In a yet further variation the guanidine carbonate has a concentration of about 5.68% to about 17.06% by weight, based on the total weight of the aqueous solution. In yet another variation the composition and hair are heated to a temperature between about 81 degrees Fahrenheit and about 122 degrees Fahrenheit. In a additional variation the composition and hair are heated for a time period of between five (5) minutes and sixty (60) minutes.

In an exemplary embodiment for a composition for use in straightening hair, the on composition is produced by combining a first and second ingredients. The first ingredient includes calcium hydroxide having a concentration of about 1.21% by weight to about 3.45% by weight, based on the total weight of the first ingredient. The second ingredient is guanidine carbonate having a concentration of about 5.68% by weight to about 17.06% by weight based on the total weight of the second ingredient. In one variation the first ingredient is an emulsion. In another variation the second ingredient is an aqueous solution. In a further variation heat is used to accelerate the production of the hair straightening composition. In yet another variation the first ingredient is an aqueous solution. In a yet further variation the second ingredient is an emulsion.

In a further exemplary composition for use in straightening hair, the composition comprises a first ingredient which includes calcium hydroxide having a concentration of about 1.21% by weight to about 3.45% by weight, based on the total weight of the first ingredient and a second ingredient which is guanidine carbonate having a concentration of about 5.68% by weight to about 17.06% by weight based on the total weight of the second ingredient. In one variation the first ingredient is an emulsion. In another variation the second ingredient is an aqueous solution. In a further variation the first ingredient is an aqueous solution. In yet another variation the second ingredient is an emulsion.

In yet another exemplary embodiment, a method of straightening hair comprising the steps of combining a first ingredient and a second ingredient to produce a hair straightening composition wherein the first ingredient is calcium hydroxide having a concentration of about 1.21% by weight to about 3.45% by weight, based on the total weight of the first ingredient and wherein the second ingredient is guanidine carbonate having a concentration of about 5.68% by weight to about 17.06% by weight based on the total weight of the second ingredient, applying the hair relaxing composition to hair, heating the hair relaxing composition and hair, and removing the product from the hair. In one variation the first ingredient is an emulsion. In another variation the second ingredient is an aqueous solution. In a further variation the composition and hair are heated to a temperature between about 81 degrees Fahrenheit and about 122 degrees Fahrenheit. In yet another variation the composition and hair are heated for a time period of between five (5) minutes and sixty (60) minutes.

In a further exemplary composition for use in straightening hair, the composition comprises an alkaline earth metal hydroxide about 0.25% by weight to about 5% by weight based on the total weight of the composition. In one variation the composition is an emulsion. In another variation the composition is an aqueous solution.

In a further exemplary embodiment, a method of straightening hair, the method comprises providing a composition including an alkaline earth metal hydroxide wherein the alkaline earth metal hydroxide is selected from the group consisting of calcium hydroxide, sodium hydroxide, barium hydroxide, lithium hydroxide, and potassium hydroxide, applying the composition to hair, heating the composition and hair and removing the composition from the hair. In a variation the alkaline earth metal hydroxide is included in an emulsion. In another variation the alkaline earth metal hydroxide is included in an aqueous solution. In a further variation the composition and hair are heated to a temperature between about 81 degrees Fahrenheit and about 122 degrees Fahrenheit. In yet another variation the composition and hair are heated for a time period of between five (5) minutes and sixty (60) minutes.

DETAILED DESCRIPTION OF THE PREFERRED EMBODIMENTS

While the invention is susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

In general the composition used for straightening hair in accordance with the present invention includes two components which react when combined to produce guanidine hydroxide. As discussed above, the use of guanidine hydroxide to straighten has been previously proposed in U.S. Pat. No. 4,304,244. One of the components of the composition used in accordance with the present invention is an alkaline earth metal hydroxide in an emulsion. Preferred hydroxides are calcium hydroxide, sodium hydroxide, lithium hydroxide, barium hydroxide, potassium hydroxide, or mixtures thereof. Calcium hydroxide is the most preferred hydroxide because it is readily available, inexpensive, and very effective. The second component of the composition used in accordance with the present invention is guanidine carbonate. The guanidine carbonate is included in an aqueous solution. Alternatively, the guanidine carbonate could be included in an emulsion and the calcium hydroxide could be included in an aqueous solution.

The two components are mixed immediately before applying the composition to the hair because guanidine hydroxide is only stable in aqueous form for about four (4) hours. The composition is prepared by mixing the aqueous guanidine carbonate and the emulsion including calcium hydroxide to initiate a reaction which produces guanidine hydroxide in the emulsion.

In the method of straightening hair according to the present invention the concentrations of the guanidine carbonate and the calcium hydroxide in the guanidine hydroxide composition used in the method are significantly lower than the concentrations used in commercially available hair straightening products such as those disclosed in U.S. Pat. No. 4,304,244. In the preferred composition of the present invention the concentration of the calcium hydroxide in the emulsion is about 1.21% by weight to about 3.45% by weight, based on the total weight of the emulsified calcium hydroxide. The concentration of the guanidine carbonate in the aqueous solution is about 5.68% by weight to about 17.06% by weight based on the total weight of the aqueous solution. In commercially available hair straightening products the concentration of calcium hydroxide in the emulsion is about 4.6% by weight, based on the total weight of the emulsion. In commercially available hair straightening products the concentration of guanidine carbonate in the aqueous solution is about 22.75% by weight, based on the total weight of the aqueous solution. The ratio of the emulsion containing the calcium hydroxide to the aqueous guanidine carbonate for the preferred composition is 4.04 to 1.

In the preferred composition of the present invention the guanidine hydroxide produced by mixing the calcium hydroxide and the guanidine carbonate has a lower concentration than the guanidine hydroxide produced in commercially available hair straightening products. The guanidine hydroxide concentration of the preferred composition is lower than the guanidine hydroxide concentration in commercially available products because the guanidine carbonate and calcium hydroxide used in the preferred composition are lower than the concentrations of guanidine carbonate and calcium hydroxide used in commercially available hair straightening products.

In the method of straightening hair according to the present invention, a hair stylist mixes the aqueous guanidine carbonate with the calcium hydroxide in the emulsion. The calcium hydroxide and guanidine carbonate react to produce guanidine hydroxide in an emulsion. The hair stylist then applies the preferred composition to the hair in the same manner as commercially available hair straightening products. In accordance with the present invention the application time of the preferred hair relaxing composition is about twenty (20) minutes. The application time is defined as the time beginning from when the composition first comes in contact with the hair to the time when all of the hair is coated with the composition.

After the hair is coated with the preferred hair relaxing composition the hair is processed for about twenty (20) minutes. The processing time is defined as the time from when all the hair is coated with the hair relaxing composition to when the hair relaxing composition is rinsed out of the hair. In accordance with the present invention the hair is heated during the processing stage. The preferred method of heating the hair is to use a commercially available hood-type hair dryer. In general, a cap is placed over the hair and the patron is placed under a hood-type hair dryer on its highest setting. Apparatus for heating the hair include hair driers, heat lamps, blow driers, hot irons, and any combination thereof. The present invention is not intended to be limited to any one type of apparatus for heating the hair.

Heating the hair while it is covered with the hair relaxing composition allows lower concentrations of guanidine carbonate and calcium hydroxide to be used. As previously discussed, the calcium hydroxide and guanidine carbonate react to form guanidine hydroxide. In commercially available hair relaxing products higher concentrations of calcium hydroxide and guanidine carbonate must be used to produce enough guanidine hydroxide to satisfactorily straighten the hair. In the present invention, lower concentrations of calcium hydroxide and guanidine carbonate can be used because the heat drives the guanidine carbonate/calcium hydroxide reaction that produces guanidine hydroxide further to completion than when the reaction takes place without heat. By heating the preferred composition during the processing time an adequate amount of guanidine hydroxide is produced to satisfactorily straighten the hair.

The lower concentrations of guanidine carbonate and calcium hydroxide allow the hair stylist applying the preferred straightening composition about twenty (20) minutes to apply the product. This is about twice the amount of time a stylist has when using commercially available hair straightening mixtures. Lower concentrations of guanidine carbonate and calcium hydroxide can be used in the preferred composition than in commercially available hydroxide-type hair relaxers because heat is added during the processing step.

After the hair relaxing composition is applied the patron is placed under a preheated hair dryer for five (5) to sixty (60) minutes depending upon the temperature of the heat. Preferably, the hair coated with the preferred composition is heated for about twenty (20) minutes at a temperature between the range of about 81 degrees Fahrenheit to about 122 degrees Fahrenheit. Generally the highest setting which the patron can comfortably tolerate is used. After the heating process the composition is rinsed out of the hair and the hair is shampooed using a neutralizing shampoo.

The application and processing time of commercially available hair straightening products is about twenty (20) minutes total. Commercially available hair straightening compositions must be removed from the hair no later than about twenty (20) minutes from the time they were first applied to the hair or very significant hair damage and scalp irritation can occur. Use of the lower concentration guanidine hydroxide and heat in the method of the present invention is an improvement over commercially available hair straightening products because its application time is about twenty (20) minutes and its processing time is about twenty (20) minutes, giving the hair stylists more time to apply and remove the composition.

The use of heat with the lower concentration calcium hydroxide and guanidine carbonate according to the present invention results in less damage to the hair than when commercially available hair relaxing products are used. Commercially available hair relaxing products having higher concentrations of calcium hydroxide and guanidine carbonate cause significant damage to the hair because the concentration of guanidine hydroxide produced by the reaction is high. The composition and method of the present invention do not damage the hair as significantly as commercially available hair straightening products because lower concentrations of calcium hydroxide and guanidine carbonate are used and the hair and composition are heated.

Due to the lower concentrations of the calcium hydroxide and guanidine carbonate and the use of heat, a barrier substance is not required when using the hair relaxing composition of the present invention. The high concentrations of calcium hydroxide and guanidine carbonate used in commercially available hair relaxing products can irritate or burn the skin. Commercially available hair relaxing products require the hair stylist to apply a barrier substance such as petrolatum to the skin surrounding the scalp and the area around the ears. The barrier substance is used to prevent the skin from becoming irritated if the hair relaxing product contacts the skin. A barrier substance is not necessary when using the composition and method of the present invention because the concentrations of calcium hydroxide and guanidine carbonate are lower and usually do not cause skin irritation.

The pH of the composition according to the present invention is lower than commercially available hair straightening products. The pH of the preferred composition is about 12.9. The pH of commercially available hair straightening products is about 13.0. The 0.1 difference in the pH of the preferred composition versus the pH of commercially available products is very significant because the pH scale is a logarithmic scale. The preferred composition is at least 20% weaker or less alkaline than the commercially available products. The composition of the present invention has a lower pH than commercially available hair straightening products because lower concentrations of guanidine carbonate and calcium hydroxide are used to make the composition. The lower pH of the composition of the present invention is an improvement over commercially available hair straightening products because skin irritation can occur when compositions having a high pH contact the skin.

An alternative composition for the hair straightening composition according to the present invention includes only an alkaline earth metal hydroxide. The alkaline earth metal hydroxide is selected from the group of sodium, lithium, potassium, and barium. The composition is single component composition. Accordingly, it is more stable than the calcium hydroxide and guanidine carbonate hair straightening composition. The alternative composition hair straightener composed of an alkaline earth metal hydroxide is usually included in an emulsion. The concentration of the alternative composition is lower than commercially available alkaline earth metal hydroxide hair straighteners. The concentration of the alternative composition is about 0.25% to 5% by weight, based on the total weight of the emulsion. The composition of commercially available alkaline earth metal hydroxide hair straightening products is about 2.0% to 2.5% by weight, based on the total weight of the emulsion.

The alternative composition is applied to the hair and heated as described above. The alternative composition is an improvement over commercially available hair straighteners because the application and processing time of the alternative composition is about twice as long as the application and processing time of commercially available hair straighteners and the pH is lower.

EXAMPLES OF THE INVENTION

While not intended to limit in any way the scope of the present invention, the following examples demonstrate embodiments of the composition and method of the present invention. The use of the compositions hereinafter disclosed is not intended to be limited in any way by the characteristics of the hair tested in the following examples.

A two-component hair relaxing composition was created with one component, Part A, being in the form of an emulsion and another component, Part B, being in the form of an aqueous solution. Three different hair relaxing compositions were created by using different mixtures of Parts A and B. The three different compositions are referred to as mixtures I, II, and III. The compositions were then tested on a number of individuals with varying hair characteristics to determine the best composition and method for varying hair types.

Example 1

The model treated for this example had the hair on her head sectioned into two separated halves and had a different mixture of Parts A and B applied to each half. Parts A and B were mixed thoroughly to produce a hair relaxing composition in an emulsion form. The characteristics of the hair for the model receiving the hair relaxing treatment were as follows:

| | |
|---|---|
| TEXTURE: | Medium |
| DENSITY: | Thick/dense |
| CURL PATTERN: | Wavy/curly |
| LENGTH: | Above shoulder |
| COLOR-TREATED: | None |
| % OF GRAY: | None |
| PRIOR STRAIGHTENING: | None |

One half of her hair was treated with mixture of Parts A and B known as mixture I having the following composition:

TABLE 1

Mixture I

| Ingredients | Weight Percent |
|---|---|
| Part A: | |
| Emulsifying Wax | 7.50 |
| Petrolatum | 12.83 |
| PPG-12-PEG-50 Lanolin | 0.99 |
| PEG-75 Lanolin | 0.01 |
| Steareth-21 | 2.25 |
| Steareth-10 | 0.01 |
| Polysorbate-60 | 0.01 |
| Mineral Oil | 15.20 |
| Propylene Glycol | 1.00 |
| R.O. Water | 44.35 |
| R.O. Water | 9.40 |
| Calcium Hydroxide | 3.45 |
| Propylene Glycol | 3.00 |
| Part B: | |
| R.O. Water | 82.79 |
| DS-49-SG | 0.02 |
| Xanthan Gum | 0.13 |
| Guanidine Carbonate | 17.06 |
| Red # 33 | 0.444 mL/lb |

The second half of her hair was treated with mixture of Parts A and B known as mixture II having the following composition:

TABLE 2

Mixture II

| Ingredients | Weight Percent |
|---|---|
| Part A: | |
| Emulsifying Wax | 7.50 |
| Petrolatum | 12.83 |
| PPG-12-PEG-50 Lanolin | 0.99 |
| PEG-75 Lanolin | 0.01 |
| Steareth-21 | 2.25 |
| Steareth-10 | 0.01 |
| Polysorbate-60 | 0.01 |
| Mineral Oil | 15.20 |
| Propylene Glycol | 1.00 |
| R.O. Water | 45.50 |
| R.O. Water | 9.40 |
| Calcium Hydroxide | 2.30 |
| Propylene Glycol | 3.00 |

TABLE 2-continued

Mixture II

| Ingredients | Weight Percent |
|---|---|
| Part B: | |
| R.O. Water | 88.48 |
| DS-49-SG | 0.02 |
| Xanthan Gum | 0.13 |
| Guanidine Carbonate | 11.37 |
| Red # 33 | 0.444 mL/lb |

The hair of the individual receiving the hair relaxing treatment was combed to remove tangles, and then the hair was sectioned. The hair relaxing mixtures I and II were applied to the appropriate section. The hair stylist examined the hair to ensure the composition was contacting the hair close to the root of the hair and combed the hair to evenly distribute the hair relaxing mixtures. When both sides of the head were covered with the hair relaxing mixtures the hair was smoothed down by hand or with a comb to assure even distribution.

The application time of the hair relaxing mixtures was about twenty (20) minutes. The application time is the time beginning from when the composition first comes in contact with the hair to the time when all of the hair is coated with the composition. After the hair is coated with the preferred hair relaxing composition the hair is processed for about twenty (20) minutes. If the stylist uses less than twenty (20) minutes to apply the hair relaxing composition, the stylist must wait until the full twenty (20) minutes have passed from the beginning of the application of the hair relaxing composition before beginning the processing step.

The processing step for this example was leaving the hair relaxing composition in the hair for twenty (20) minutes. No heat was applied in the processing step. Following the processing step the hair was shampooed twice using a neutralizing shampoo and rinsed thoroughly. Moisturizing conditioner was then applied to the model's hair. The hair was then rinsed again thoroughly. Detangling spray was then applied to the model's hair and the hair was combed with a wide-tooth comb. The model was then placed under a hood-type hair dryer until the hair was damp to almost dry. The model was advised not to shampoo the hair for 24–48 hours and was given products to maintain the hair relaxing treatment. Finally the models hair was analyzed for post-treatment hair characteristics.

Immediately after the hair relaxing treatment, the hair was analyzed to determine the straightness of the hair and the damage to the hair. For this example, the hair was straight after the hair relaxing treatment. There was very little difference between the two sides of the head, although the hair treated with mixture I felt slightly drier than the hair treated with mixture II. The left side using mixture II appeared to lay closer to the head. The model's hair was analyzed again two weeks after the hair relaxing treatment. The side using mixture I appeared visibly straighter than the side using mixture II, although the hair treated with mixture I appeared in a slightly worse condition than the hair treated with mixture II. The conclusion was that mixture I straightened hair better than mixture II, but also risked more damage to the hair.

Example 2

Example 1 was repeated on a different model, with the addition of heat during the processing step. The characteristics of the hair for the model used for this example are as follows:

| | |
|---|---|
| TEXTURE: | Coarse |
| DENSITY: | Thick/dense |
| CURL PATTERN: | Wavy/curly |
| LENGTH: | Beyond shoulder |
| COLOR-TREATED: | Permanent |
| % OF GRAY: | None |
| PRIOR STRAIGHTENING | None |

The hair relaxing treatment was carried out with the same procedure as Example 1, except that a cap was placed over the hair and the hair was heated during the processing stage under a hood-type hair dryer on its highest setting. The steps following the processing step were the same as the steps following the processing step in Example 1. The post-treatment analysis of the hair revealed that the hair was straight, although the side using mixture I felt slightly drier. The model returned two weeks after the hair relaxing treatment for hair analysis. The hair treated with mixture I was visibly straighter than the hair treated with mixture II. The hair on the side treated with mixture I was more damaged than the hair treated with mixture II. The conclusion was that mixture I did straighten hair better, but also risked significant damage to the hair. The addition of heat from the hair dryer seemed to be effective and did not seem to cause unreasonable damage to the hair.

Example 3

Example 3 is the same as Example 2 except only one mixture was used on all of the model's hair rather than separating the hair into two separate halves. The hair characteristics of the model were as follows:

| | |
|---|---|
| TEXTURE: | Medium |
| DENSITY: | Thick/dense |
| CURL PATTERN: | Wavy/curly |
| LENGTH: | Beyond shoulder |
| COLOR-TREATED: | None |
| % OF GRAY: | None |
| PRIOR STRAIGHTENING | None |

Mixture II was used for this example. Heat was applied during the twenty (20) minute processing step by a hood-type hair dryer. Analysis of the hair immediately after the hair relaxing treatment showed the hair was straightened in a satisfactory manner with minimal damage. The analysis of the hair two weeks after the service showed that the hair had reverted slightly from the day of service. It was concluded that mixture II with heat seemed to do an acceptable job of straightening the hair and leaving the hair in good condition. The conclusion was that mixture I may work better for individuals who have not had their hair colored.

Example 4

Example 4 is the same as Example 3, but with a different model. The hair characteristics of the model receiving the hair relaxing treatment are as follows:

| | |
|---|---|
| TEXTURE: | Medium |
| DENSITY: | Thick/dense |
| CURL PATTERN: | Slightly wavy |
| LENGTH: | Above shoulder |
| COLOR-TREATED: | Permanent |
| % OF GRAY: | None |
| PRIOR STRAIGHTENING | None |

Analysis of the hair immediately after the hair relaxing treatment showed the hair was straightened in a satisfactory manner with minimal damage. The model stated that the hair felt less thick and heavy. The analysis of the hair two weeks after the hair relaxing treatment showed that the hair was in good condition, although it felt a bit dry and perceptively dry to the touch. The conclusion was that mixture II with the addition of heat yields very good hair straightening and very little damage to the hair.

Example 5

The model used for this example had the following hair characteristics:

| | |
|---|---|
| TEXTURE: | Fine |
| DENSITY: | Normal |
| CURL PATTERN: | Slightly wavy |
| LENGTH: | Beyond shoulder |
| COLOR-TREATED: | Highlighted |
| % OF GRAY: | None |
| PRIOR STRAIGHTENING | None |

Example 1 was repeated, except a different mixture was used. One side of the model's hair was treated with mixture of Parts A and B, known as the III mixture having the following composition:

TABLE 3

| Mixture III | |
|---|---|
| Ingredients | Weight Percent |
| Part A: | |
| Emulsifying Wax | 7.50 |
| Petrolatum | 12.83 |
| PPG-12-PEG-50 Lanolin | 0.99 |
| PEG-75 Lanolin | 0.01 |
| Steareth-21 | 2.25 |
| Steareth-10 | 0.01 |
| Polysorbate-60 | 0.01 |
| Mineral Oil | 15.20 |
| Propylene Glycol | 1.00 |
| R.O. Water | 46.59 |
| R.O. Water | 9.40 |
| Calcium Hydroxide | 1.21 |
| Propylene Glycol | 3.00 |
| Part B: | |
| R.O. Water | 94.17 |
| DS-49-SG | 0.02 |
| Xanthan Gum | 0.13 |
| Guanidine Carbonate | 5.68 |
| Red # 33 | 0.444 mL/lb |

The other side of the model's hair was treated with mixture of Parts A and B, known as mixture I shown in Example 1, TABLE 1. As in Example 1, the hair was not heated in the processing step.

Analysis of the hair immediately after the hair relaxing treatment showed that the hair treated with mixture I was very straight while the hair treated with mixture III was in better condition, but not acceptably straight. Two weeks after the relaxing treatment, the hair was again analyzed. The hair treated with mixture I was much straighter, but perceptively dry to the touch. The hair treated with mixture III was in better condition than the hair treated with mixture I, but was not nearly as straight.

Example 6

Example 4 was repeated using a model having the following hair characteristics:

| TEXTURE: | Medium |
|---|---|
| DENSITY: | Thick/dense |
| CURL PATTERN: | Wavy/curly |
| LENGTH: | Beyond shoulder |
| COLOR-TREATED: | Permanent |
| % OF GRAY: | None |
| PRIOR STRAIGHTENING | None |

The model's hair was treated with a mixture of Parts A and B known as mixture III shown in Example 5, TABLE 3. Heat was applied to the hair during the twenty (20) minute processing time. Analysis of the hair immediately after the hair relaxing treatment showed the hair was much less full and slightly straighter. Analysis of the hair two weeks after the relaxing treatment showed that the hair was slightly straighter and more manageable than before the treatment. However, the conclusion was that the level of straightness of the hair was unacceptable and mixture III with the addition of heat did not produce satisfactory results.

Example 7

Example 4 was repeated except mixture II was used. One side of the model's head was heated during the processing period, and the other side was left exposed to ambient air during the duration of the processing period. The model used for this example had the following hair characteristics:

| TEXTURE: | Fine |
|---|---|
| DENSITY: | Thin |
| CURL PATTERN: | Wavy/curly |
| LENGTH: | Shoulder |
| COLOR-TREATED: | Semi-permanent |
| % OF GRAY: | None |
| PRIOR STRAIGHTENING | None |

For this test, the left side of the model's head was covered with a bonnet and a portable hair dryer was used to heat the hair during the twenty (20) minute processing time. The right side of the model's hair was left exposed to the air for the twenty (20) minute processing time. Analysis of the hair immediately after the hair relaxing treatment showed very little difference between the hair which had been heated during the processing time and the hair that had not been heated during the processing time. One week after the hair relaxing treatment, the model returned to the testing facility and the hair was again analyzed. The hair that had been heated during the processing step was slightly straighter than the hair that had not been heated. This model appeared to have fairly wavy hair, even after the treatment. It was concluded that this model may have benefitted from the use of mixture I because it produces more guanidine hydroxide, the straightening agent.

Example 8

Example 7 was repeated, except a processing time of thirty (30) minutes was used. The left side of the model's head was covered with a bonnet and a portable hair dryer was used to apply heat for the duration of the processing time. The right side of the model's head was exposed to ambient air for the duration of the processing time. The model used for this example had the following hair characteristics:

| TEXTURE: | Coarse |
|---|---|
| DENSITY: | Thick |
| CURL PATTERN: | Wavy/curly |
| LENGTH: | Shoulder |
| COLOR-TREATED: | Permanent |
| % OF GRAY: | Up to 20 |
| PRIOR STRAIGHTENING | None |

The analysis of the hair immediately after the hair relaxing treatment showed the hair subjected to heat during the processing step was much more straight than the non-heated hair. One week after the hair relaxing treatment the model was brought back in and the hair was again analyzed. The hair that had been subjected to heat during the processing step was much straighter and more manageable. The condition of the hair that had been heated was very similar to the condition of the hair that had not been heated. The thirty (30) minute processing time was very effective, but thirty (30) minutes was determined to be too long in terms of acceptable length of a salon service. It was determined that all tests from this point on will use a twenty (20) minute application time and a twenty (20) minute processing time.

Example 9

Example 8 was repeated except a ten (10) minute application and ten (10) minute processing time were used. The model used for this example had the following hair characteristics:

| TEXTURE: | Fine |
|---|---|
| DENSITY: | Normal |
| CURL PATTERN: | Wavy/curly |
| LENGTH: | Above shoulder |
| COLOR-TREATED: | Permanent |
| % OF GRAY: | Up to 20 |
| PRIOR STRAIGHTENING | None |

The left side of the model's head was covered with a bonnet of a portable hair dryer and heated for ten (10) minutes. The right side of the model's head was left to exposed to ambient air for the ten (10) minute processing time. Analysis of the hair immediately after the hair relaxing treatment showed the heat processed side appeared slightly more straight than the non-heated side. One week after the hair relaxing service, the model was brought back in and hair was analyzed. The hair subjected to heat during the processing stage was much straighter and more manageable than the hair not subjected to heat during the processing step. The condition and feel of the hair that had been heated and the hair that had not been heated were about the same. It was determined that a twenty (20) minute processing time produced better results than ten (10) minute or thirty (30) minute processing times.

Example 10

Mixture I was applied to the right side of the model's hair and mixture II was applied to the left side of the model's hair. The application time was twenty (20) minutes. The model's hair had the following characteristics:

| | |
|---|---|
| TEXTURE: | Coarse |
| DENSITY: | Thick |
| CURL PATTERN: | Slightly wavy |
| LENGTH: | Beyond shoulder |
| COLOR-TREATED: | Highlighted |
| % OF GRAY: | None |
| PRIOR STRAIGHTENING | None |

The hair was heated during the twenty (20) minute processing step. The hair was then shampooed twice using neutralizing shampoo and rinsed throughly. Moisturizing conditioner was then applied and the hair was rinsed throughly. A hair conditioner was applied next. The model was placed under a hair dryer with a hair drying cap for five (5) minutes. The hair was then rinsed and detangling spray was applied to the model's hair. The hair was combed through with a wide tooth comb and the model was placed under a dryer until the hair was damp to almost dry. The model was advised not to shampoo the hair for 24 to 48 hours and was given products to maintain the treatment.

Analysis of the hair immediately after treatment showed there was no significant difference between the hair treated with mixture I versus mixture II. Three days after the hair relaxing treatment, the model was brought back in and the hair was analyzed to determine the differences between mixture I and mixture II in terms of straightness and condition. The hair treated with mixture I appeared straighter although the hair was perceptively dryer than the hair treated with mixture II. The hair dryer appeared to neither help nor hurt the condition of the hair.

Example 11

Example 2 was repeated. The model used for this example had the following hair characteristics:

| | |
|---|---|
| TEXTURE: | Fine |
| DENSITY: | Normal |
| CURL PATTERN: | Slightly wavy |
| LENGTH: | Beyond shoulder |
| COLOR-TREATED: | Semi-permanent |
| % OF GRAY: | Up to 20 |
| PRIOR STRAIGHTENING | None |

Mixture I was used on the right side of the model's hair and mixture II was used on the left side of the model's hair. The application time was twenty (20) minutes. The hair was heated during the twenty (20) minute processing time. The hair was analyzed immediately following the hair relaxing treatment. The hair treated with mixture I appeared slightly more straight. Three days after the hair relaxing treatment the model was brought back in and the hair was analyzed. The hair treated with mixture I appeared much straighter than the hair treated with mixture II. The hair treated with mixture I was slightly more dry, especially on the ends.

Example 12

Example 11 was repeated. The model's hair had the following characteristics:

| | |
|---|---|
| TEXTURE: | Fine |
| DENSITY: | Normal |
| CURL PATTERN: | Slightly wavy |
| LENGTH: | Beyond shoulder |
| COLOR-TREATED: | Semi-permanent |
| % OF GRAY: | None |
| PRIOR STRAIGHTENING | None |

Mixture I was applied to the right side of the model's hair and mixture II was applied to the left side of the model's hair. The application time was twenty (20) minutes. Heat was applied to the hair during the twenty (20) minute processing step. The hair was then shampooed twice with a neutralizing shampoo and rinsed throughly. Moisturizing conditioner was the applied and then hair was rinsed throughly. A second hair conditioner was then applied. The model was placed under a dryer with a hair drying cap for five (5) minutes. The hair was then rinsed and detangling spray was applied to the model's hair. The hair was combed through with a wide tooth comb and the model was placed under a hair dryer until the hair was damp to dry. The model was advised not to shampoo the hair for 24 to 48 hours and was given products to maintain the hair relaxing treatment.

The hair was analyzed immediately after the hair relaxing treatment. There was very little difference between the hair treated with mixture I and the hair treated with mixture II. Three days after the hair relaxing treatment the model was brought in and the hair was analyzed to determined the differences between mixture I and mixture II in terms of straightness and condition. The hair treated with mixture I appeared straighter and less full than the hair treated with mixture II. The hair treated with mixture I was slightly more dry than the hair treated with mixture II. It was determined that the second hair conditioner may cause hair damage.

Examples 1 through 12 indicate the best hair straightening resulted when mixture I or II were used and heat was added during the processing stage. Hair straightening mixtures I and II produced good results, i.e., straighter hair, when used with a twenty (20) minute application time and a twenty (20) minute processing time when heat was used during the processing step. The examples indicated mixture I produced the best results when the hair is very curly and has not been color treated recently. Mixture II produced the best results when used on hair that is naturally less curly or slightly damaged from a hair treatment such as hair coloring.

What is claimed is:

1. A method of straightening hair, the method comprising;
    applying a composition to hair, the composition including an alkaline earth metal hydroxide and guanidine carbonate included in an aqueous solution wherein the alkaline earth metal hydroxide is selected from the group consisting of calcium hydroxide, sodium hydroxide, barium hydroxide, lithium hydroxide, and potassium hydroxide, the guanidine carbonate having a concentration of about 5.68% to about 17.06% by weight, based on the total weight of the aqueous solution;
    heating the composition and hair; and
    removing the composition from the hair.
2. The method of claim 1, wherein the alkaline earth metal hydroxide is included in an emulsion.

3. The method of claim 1, wherein the composition and hair are heated by a hooded hair dryer.

4. The method of claim 2, wherein the alkaline earth metal hydroxide has a concentration of about 1.21% by weight to about 3.45% by weight, based on the total weight of the emulsion.

5. The method of claim 1, wherein the composition is removed from the hair by rinsing the hair with water.

6. The method of claim 1, wherein the composition and hair are heated to a temperature between about 81 degrees Fahrenheit and about 122 degrees Fahrenheit.

7. The method of claim 1, wherein the composition and hair are heated for a time period of between five (5) minutes and sixty (60) minutes.

8. The method of claim 6, wherein the composition and hair are heated for a time period of between five (5) minutes and sixty (60) minutes.

9. The method of claim 7, wherein the composition and hair are heated to a temperature between about 81 degrees Fahrenheit and about 122 degrees Fahrenheit.

10. The method of claim 1, wherein the hair is rinsed with water and shampooed to remove the composition from the hair.

11. The method of claim 10, wherein the alkaline earth metal hydroxide has a concentration of about 1.21% by weight to about 3.45% by weight, based on the total weight of the emulsion.

12. The method of claim 10, wherein a shampoo having a pH of between 4 and 6 is used to shampoo the hair.

13. The method of claim 10, wherein the composition and hair are heated to a temperature between about 81 degrees Fahrenheit and about 122 degrees Fahrenheit.

14. The method of claim 10, wherein the composition and hair are heated for a time period of between five (5) minutes and sixty (60) minutes.

15. The method of claim 3, wherein the alkaline earth metal hydroxide is included in an emulsion.

16. The method of claim 15, wherein the alkaline earth metal hydroxide has a concentration of about 1.21% by weight to about 3.45% by weight, based on the total weight of the emulsion.

17. The method of claim 16, wherein the composition and hair are smoothed using a comb prior to heating the composition and hair.

18. The method of claim 15, wherein the composition and hair are heated to a temperature between about 81 degrees Fahrenheit and about 122 degrees Fahrenheit.

19. The method of claim 15, wherein the composition and hair are heated for a time period of between five (5) minutes and sixty (60) minutes.

20. A composition for use in straightening hair consisting of:
    a first ingredient which includes calcium hydroxide having a concentration of about 1.21% by weight to about 3.45% by weight, based on the total weight of the first ingredient;
    a second ingredient which includes guanidine carbonate having a concentration of about 5.68% by weight to about 17.06% by weight, based on the total weight of the second ingredient; and
    wherein the first ingredient and the second ingredient are combined to produce a hair straightening composition.

21. The composition of claim 20, wherein the first ingredient is an emulsion.

22. The composition of claim 20, wherein the second ingredient is an aqueous solution.

23. The composition of claim 20, wherein heat is used to accelerate the production of the hair straightening composition.

24. The composition of claim 20, wherein the first ingredient is an aqueous solution.

25. The composition of claim 20, wherein the second ingredient is an emulsion.

26. A composition for use in straightening hair consisting of:
    a first ingredient which includes calcium hydroxide having a concentration of about 1.21% by weight to about 3.45% by weight, based on the total weight of the first ingredient; and
    a second ingredient which includes guanidine carbonate having a concentration of about 5.68% by weight to about 17.06% by weight based on the total weight of the second ingredient.

27. The composition of claim 26, wherein the first ingredient is an emulsion.

28. The composition of claim 26, wherein the second ingredient is an aqueous solution.

29. The composition of claim 26, wherein the first ingredient is an aqueous solution.

30. The composition of claim 26, wherein the second ingredient is an emulsion.

31. A method of straightening hair, the method comprising:
    combining a first ingredient and a second ingredient to produce a hair straightening composition wherein the first ingredient is calcium hydroxide having a concentration of about 1.21% by weight to about 3.45% by weight, based on the total weight of the first ingredient and wherein the second ingredient is guanidine carbonate having a concentration of about 5.68% by weight to about 17.06% by weight based on the total weight of the second ingredient;
    applying the hair straightening composition to hair;
    heating the hair straightening composition and hair; and
    removing the hair straightening composition from the hair.

32. The method of claim 31, wherein the first ingredient is an emulsion.

33. The method of claim 31, wherein the second ingredient is an aqueous solution.

34. The method of claim 31, wherein the composition and hair are heated to a temperature between about 81 degrees Fahrenheit and about 122 degrees Fahrenheit.

35. The method of claim 31, wherein the composition and hair are heated for a time period of between five (5) minutes and sixty (60) minutes.

36. The method of claim 32, wherein the second ingredient is an aqueous solution.

37. The method of claim 32, wherein the composition and hair are heated to a temperature between about 81 degrees Fahrenheit and about 122 degrees Fahrenheit.

38. The method of claim 36, wherein the composition and hair are heated for a time period of between five (5) minutes and sixty (60) minutes.

39. A composition for use in straightening hair comprising:
    an alkaline earth metal hydroxide having a concentration of about 0.25% by weight to about 5% by weight based on the total weight of the composition, the composition configured to straighten hair when heated.

40. The composition of claim 39, wherein the composition is an emulsion.

41. The composition of claim 39, wherein the composition is an aqueous solution.

42. A method of straightening hair, the method comprising;

providing a composition including an alkaline earth metal hydroxide wherein the alkaline earth metal hydroxide is selected from the group consisting of calcium hydroxide, sodium hydroxide, barium hydroxide, lithium hydroxide, and potassium hydroxide, applying the composition to hair;

heating the composition and hair; and removing the composition from the hair.

43. The method of claim 42, wherein the alkaline earth metal hydroxide is included in an emulsion.

44. The method of claim 42, wherein the alkaline earth metal hydroxide is included in an aqueous solution.

45. The method of claim 42, wherein the composition and hair are heated to a temperature between about 81 degrees Fahrenheit and about 122 degrees Fahrenheit.

46. The method of claim 42, wherein the composition and hair are heated for a time period of between five (5) minutes and sixty (60) minutes.

47. The method of claim 43, wherein the composition and hair are heated to a temperature between about 81 degrees Fahrenheit and about 122 degrees Fahrenheit.

48. The method of claim 43, wherein the composition and hair are heated for a time period of between five (5) minutes and sixty (60) minutes.

49. The method of claim 44, wherein the composition and hair are heated to a temperature between about 81 degrees Fahrenheit and about 122 degrees Fahrenheit.

50. The method of claim 44, wherein the composition and hair are heated for a time period of between five (5) minutes and sixty (60) minutes.

51. A method of treating hair, the method comprising;

applying a composition to hair, the composition including an alkaline earth metal hydroxide and guanidine carbonate included in an aqueous solution wherein the alkaline earth metal hydroxide is selected from the group consisting of calcium hydroxide, sodium hydroxide, barium hydroxide, lithium hydroxide, and potassium hydroxide, the guanidine carbonate having a concentration of about 5.68% to about 17.06% by weight, based on the total weight of the aqueous solution;

heating the composition and hair; and removing the composition from the hair.

52. The method of claim 51, wherein the hair is substantially straightened.

53. The method of claim 51, wherein the hair is substantially relaxed.

54. A composition for use in treating hair comprising:

a first ingredient which includes calcium hydroxide having a concentration of about 1.21% by weight to about 3.45% by weight, based on the total weight of the first ingredient; and a second ingredient which includes guanidine carbonate having a concentration of about 5.68% by weight to about 17.06% by weight based on the total weight of the second ingredient.

55. The composition of claim 54, wherein the hair is substantially straightened.

56. The composition of claim 54, wherein the hair is substantially relaxed.

57. A method of treating hair, the method comprising:

providing a composition including an alkaline earth metal hydroxide wherein the alkaline earth metal hydroxide is selected from the group consisting of calcium hydroxide, sodium hydroxide, barium hydroxide, lithium hydroxide, and potassium hydroxide, applying the composition to hair;

heating the composition and hair; and removing the composition from the hair.

58. The method of claim 57, wherein the hair is substantially straightened.

59. The method of claim 57, wherein the hair is substantially relaxed.

60. A method of treating hair, the method comprising the steps of:

providing a composition including an alkaline earth metal hydroxide and guanidine carbonate wherein the alkaline earth metal hydroxide is selected from the group consisting of calcium hydroxide, sodium hydroxide, barium hydroxide, lithium hydroxide, and potassium hydroxide, the composition having a first pH;

applying the composition to the hair;

heating the composition and the hair, the composition having a second pH, the second pH higher than the first pH; and removing the composition from the hair.

61. The method of claim 60, wherein the hair is substantially straightened.

62. The method of claim 60, wherein the hair is substantially relaxed.

* * * * *